ical Patent (12) United States Patent Davis

(10) Patent No.: US 7,594,507 B2
(45) Date of Patent: Sep. 29, 2009

(54) THERMAL GENERATION OF DROPLETS FOR AEROSOL

(75) Inventor: Colin C. Davis, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 2083 days.

(21) Appl. No.: 09/761,287

(22) Filed: Jan. 16, 2001

(65) Prior Publication Data

US 2002/0092519 A1 Jul. 18, 2002

(51) Int. Cl.
*A61M 11/00* (2006.01)
*F23D 11/00* (2006.01)
*F23D 14/00* (2006.01)
*A61M 16/00* (2006.01)

(52) U.S. Cl. ............................ 128/200.14; 128/200.23; 128/203.26

(58) Field of Classification Search ............ 128/200.14, 128/200.18, 200.23, 203.15, 203.26, 200.16, 128/203.12, 204.23; 438/21; 216/27
See application file for complete search history.

(56) References Cited

U.S. PATENT DOCUMENTS

| | | | | |
|---|---|---|---|---|
| 3,900,138 | A * | 8/1975 | Phillips | 222/340 |
| 5,261,601 | A * | 11/1993 | Ross et al. | 239/102.2 |
| 5,305,015 | A | 4/1994 | Schantz | |
| 5,487,378 | A * | 1/1996 | Robertson et al. | 128/200.16 |
| 5,547,094 | A | 8/1996 | Bartels et al. | |
| 5,608,436 | A | 3/1997 | Baughman | |
| 5,666,977 | A * | 9/1997 | Higgins et al. | 131/194 |
| 5,881,716 | A * | 3/1999 | Wirch et al. | 128/200.16 |
| 5,894,841 | A * | 4/1999 | Voges | 128/203.12 |
| 6,000,787 | A | 12/1999 | Weber | |
| 6,082,854 | A | 7/2000 | Axtell | |
| 6,084,609 | A | 7/2000 | Manini | |
| 6,099,108 | A | 8/2000 | Weber | |
| 6,113,221 | A | 9/2000 | Weber | |
| 6,123,070 | A | 9/2000 | Bruna | |
| 6,126,276 | A | 10/2000 | Davis | |
| 6,155,670 | A | 12/2000 | Weber et al. | |
| 6,299,270 | B1 * | 10/2001 | Merrill | 347/9 |
| 6,354,694 | B1 * | 3/2002 | Weber et al. | 347/48 |
| 6,443,146 | B1 * | 9/2002 | Voges | 128/200.14 |
| 6,629,524 | B1 * | 10/2003 | Goodall et al. | 128/200.14 |
| 6,723,077 | B2 * | 4/2004 | Pickup et al. | 604/305 |
| 6,830,046 | B2 * | 12/2004 | Blakley et al. | 128/200.14 |
| 7,125,731 | B2 * | 10/2006 | Haluzak et al. | 438/21 |
| 2004/0016427 | A1 * | 1/2004 | Byron et al. | 128/200.14 |
| 2005/0150489 | A1 * | 7/2005 | Dunfield et al. | 128/200.14 |

FOREIGN PATENT DOCUMENTS

| | | |
|---|---|---|
| EP | 0 706 352 | 1/1995 |
| EP | 0 940 257 | 9/1999 |
| EP | 0 940 257 A2 | 9/1999 |
| EP | 0 953 445 | 11/1999 |
| EP | 1 005 917 | 6/2000 |
| EP | 1 066 850 | 1/2001 |
| WO | WO 00/50111 | 8/2000 |

* cited by examiner

*Primary Examiner*—Danton DeMille

(57) ABSTRACT

A thermal-type drop generator having a geometry that is configured so that the ejection of liquid from the chamber has the effect of separating the ejected volume into a number of small droplets. The relationship between the thickness of the liquid chamber and the area of the heat transducer used to eject the liquid is controlled to provide the separating aspect so that the resultant droplets have very small volumes, in the range of tens of femtoliters. Such small droplets are readily entrained in an aerosol and especially useful for pulmonary delivery of medicinal fluid.

5 Claims, 4 Drawing Sheets

THERMAL GENERATION OF DROPLETS FOR AEROSOL

TECHNICAL FIELD

This invention relates to the generation of liquid droplets that are suitably sized for entrainment in aerosols.

BACKGROUND AND SUMMARY OF THE INVENTION

The ongoing advances in medicine and biotechnology are providing many effective and promising systemic therapies that call for the delivery of biological and chemical substances (such as peptides, proteins, and small molecules) to the patient's bloodstream. There are various problems associated with getting certain substances to the bloodstream by conventional delivery means, such as transdermal and oral. For instance, oral delivery of therapeutic proteins does not work because the proteins are digested before they have an opportunity to reach the bloodstream. Thus, for this and other reasons, it is best to deliver such substances to the bloodstream by as direct a route as possible.

An aerosol is a gaseous suspension of very fine solid or liquid particles. Aerosols are presently used for delivering certain drugs to a patient's lungs. Delivery of drugs or other therapeutic substances to a patient's lungs is sometimes referred to as pulmonary delivery.

The innermost tissue of the lung is know as the alveolar epithelium, which comprises hundreds of millions of tiny air sacs, called alveoli, that are surrounded by a large network of blood capillaries. The alveoli walls are a thin, single cellular layer that enables rapid absorption of fluids from the alveoli to the bloodstream. Most effective pulmonary delivery is accomplished when the substance is delivered to the alveoli. The delivery process requires the generation of very small particles or droplets that can be entrained in a gas as an aerosol and inhaled by the patient into the alveoli for transfer to the bloodstream.

The lung's alveoli can readily absorb liquid drops having diameters of about 4 µm, which represents a volume of 33.5 femtoliters. A femtoliter is one quadrillionth ($10^{-15}$) of a liter. Larger drops tend to contact the lung walls before reaching the alveoli and are less likely to permeate the wall to the bloodstream because the airway to the alveoli is lined with a thick, ciliated mucus-covered cell layer.

A popular pulmonary delivery mechanism is known as a metered dose inhaler (MDI). These are widely used for the delivery of asthma medication. While an MDI delivery system may be effective for medications designed to medicate the lung tissue, they are not optimal for delivery of substances to the alveoli (hence, to the bloodstream). In this regard, an MDI typically combines the drug with a propellant in a pressurized container. Actuation of the device releases metered doses of the aerosol, but the droplet size distribution is large, and the vapor pressure of the propellant varies with temperature and number of uses. Thus, the behavior of the material in the air stream and the extent to which droplets reach the alveoli becomes somewhat unpredictable.

In view of the foregoing, it can be appreciated that there is a need for a droplet generator that can reliably produce very small-volume droplets with a generally uniform size distribution for entrainment in aerosols.

One reference, U.S. Pat. No. 5,894,841, has recognized the potential of generating very small droplets using a drop generator that is adapted from the kind employed in ink-jet printing. The type of ink-jet printing of interest here (often called thermal ink-jet printing) conducts ink into tiny chambers. Each chamber includes a heat transducer such as, for example, a thin-film resistor to create a vapor bubble that ejects a droplet of ink through an orifice that overlies the chamber. The chambers and orifices are incorporated into a printhead device that is connected with a supply of ink and with a controller for timing the droplet ejection to reproduce images on media. The just-mentioned reference does not provide particulars of a thermally efficient drop generator for creating the femtoliter-size drops that are desirable for effective pulmonary delivery.

As respects drop generators such as those used with thermal ink-jet printing, orifice size is but one factor for controlling the size of the droplet volume that is expelled with each activation of the resistor (or other suitable heat transducer). Much greater roles are played by the configuration of the ink chamber that is associated with the orifice, as well as the size and energy-producing capabilities of the heat transducer in the chamber.

Current ink-jet designs provide drop generators that produce droplet volumes as small as 4 picoliters, which is equivalent to 4,000 femtoliters. In order to produce droplets in the range of tens of femtoliters that can be entrained, for example, in an aerosol for delivery of the droplets to the alveoli, one is confronted with several problems that prevent a simple scaling-down of current designs to arrive at such small droplet volumes.

For example, ejection of single droplets in the tens of femtoliters size range would require extremely small ink chambers and resistors, having critical dimensions that would be difficult to fabricate and control with conventional ink-jet printhead manufacturing processes. Even if such fabrication were undertaken, such small resistors would likely be thermally inefficient. The heat loss (that is, energy not transferred to the ink in the course of forming a vapor bubble) from such small resistors would have to be overcome with a relatively higher amount of energy (called turn-on-energy, or TOE) for forming the vapor bubble. Increasing the TOE generates more stress in the heat transducer, which tends to lower reliability of the transducer over time.

The present invention is directed to a thermal-type drop generator having a geometry that is configured so that the ejection of the liquid from the chamber has the effect of separating the ejected volume into a number of small droplets. This provides a thermally efficient drop generator (as compared to one that is scaled to produce a single small droplet for each activation of the heat transducer) and generally avoids the need for meeting difficult manufacturing tolerances as discussed above.

In one preferred embodiment of the present invention the relationship between the thickness of the liquid chamber and the area of the heat transducer is controlled to provide the separating aspect mentioned above.

The ejection of the liquid is readily controlled for precise metering of the amount of droplets ejected. It will be appreciated, therefore, that the thermal generation of droplets contemplated by the present invention provides in a single action (that is, the controlled "firing" of the heat transducer to expel the contents of the liquid chamber) both the metering of the amount of liquid expelled, as well as the generation of suitably small droplets. That is, the firing of liquid from the chamber need not be accompanied with other mechanisms for reducing the volume of ejected liquid to suitably small droplets.

As another aspect of this invention, the volume of liquid in a chamber is expelled through a number of orifices using the volume-separating aspect mentioned above. This has the effect of multiplying (relative to a single-orifice embodiment) the number of droplets produced each time the heat transducer is activated.

Apparatus and methods for carrying out the invention are described in detail below. Other advantages and features of the present invention will become clear upon review of the following portions of this specification and the drawings.

DETAILED DESCRIPTION OF PREFERRED EMBODIMENTS

Figure 1:
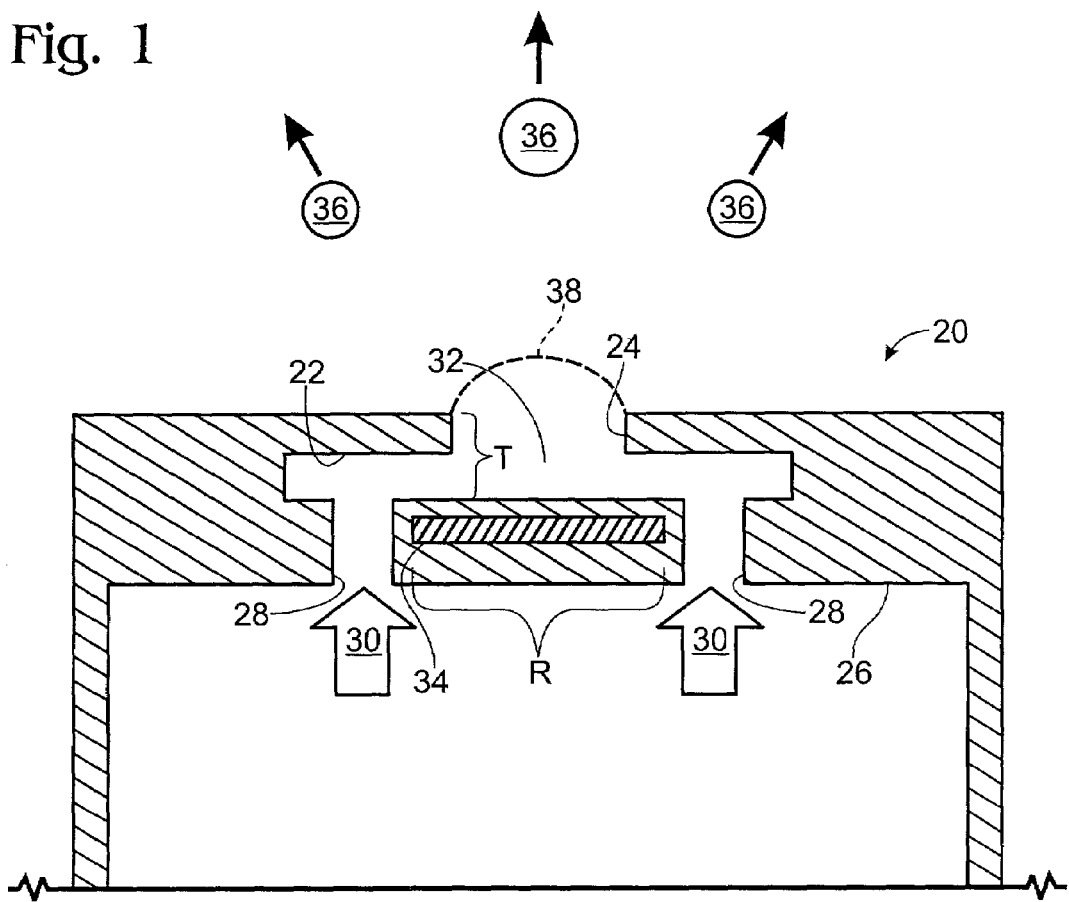
FIG. 1 is a reproduction of a graphic from a computational fluid dynamics simulation of the performance of a drop generator configured in accordance with the present invention.

FIG. 1 is a reproduction of a graphic from a computational fluid dynamics simulation of the performance of a drop generator that is formed in accordance with one aspect of the present invention. In that figure, the drop generator 20 is depicted in cross section. For modeling purposes, a solid orifice structure 22 is constructed as a generally planar member having a circular orifice 24 defined in it.

The orifice structure is continuous with a solid substrate member 26 that underlies the orifice structure and has its opposing side in communication with a liquid. Two inlets 28 are defined in the substrate to allow the liquid to flow (as depicted by arrows 30) into a chamber 32. The chamber 32 is a small reservoir for holding liquid prior to ejection of the liquid from the chamber through the orifice 24.

The mechanism for ejecting the liquid from the chamber is a heat transducer 34 that generates in the liquid-filled chamber a vapor bubble, the expansion of which ejects the liquid. For computational purposes the heat transducer 34 is considered a planar member (such as a thin-film resistor) that, upon actuation, provides an energy density of about 4 $nJ/m^2$. The liquid under consideration has a viscosity of about 3 cp and a boiling point of 100° C.

In accordance with the present invention, the relationship between the configuration of the chamber 32 and the energy provided by the heat transducer 34 is controlled for ejecting two or more femtoliter-sized droplets 36 with each activation of the heat transducer 34. In one implementation of this relationship, the thickness of the chamber and the area of the heat transducer are selected so that the front of the transducer-generated vapor bubble (depicted as dashed line 38 in FIG. 1) expands to protrude from the chamber, and thus vent to ambient, by an amount sufficient to force all of the liquid from the chamber. Moreover, because the chamber is relatively thin, as described more fully below, the liquid ejected from the chamber separates into droplets 36, each droplet comprising a fraction of the volume of liquid ejected from the chamber. As depicted in FIG. 1, the trajectories of the droplets are generally divergent.

One technique for arriving at a relationship between the configuration of the chamber 32 and the energy provided by the heat transducer 34 for ejecting the entire liquid chamber contents in the form of separate droplets 36 is to make the chamber relatively thin with respect to the area of the transducer.

For instance, the dimension "T" in FIG. 1 represents the thickness of the chamber, and the dimension "R" is a length dimension of the heat transducer (more generally, and assuming a square transducer in this illustration, R is the square root of the area of the heat transducer). In one embodiment, the dimensionless parameter comprising the ratio of the chamber thickness "T" to the square root of the transducer area "R" is selected to be less than about 0.75, preferably less than 0.50, and most preferably about 0.35. In such an instance, droplets averaging about 33 femtoliters in volume (about 4 μm in diameter) are generated, which, as noted above, are readily entrained in an aerosol and ideal for pulmonary delivery.

What follows is a description of one preferred approach to fabricating drop generators in accordance with the relationship just discussed.

FIG. 2 shows a greatly enlarged cross section of one drop generator 20 formed in accordance with the present invention. For illustrative purposes only one drop generator is shown, but, as will become clear, the fabrication process allows the production of multiple drop generators. The number of drop generators produced depends upon the amount of droplets that are required for a given application. One can consider this requirement in terms of flux, or the number of droplets simultaneously ejected from the drop generators. For greater flux requirements, more drop generators are fabricated.

The exemplary drop generator 20 includes a rigid substrate 40 that can be a silicon base 42, which is preferably a conventional silicon wafer upon which has been grown an insulation layer, such as silicon dioxide. The substrate 40 may be as described in the prior art relating to ink-jet printing, such as U.S. Pat. No. 4,719,477, hereby incorporated by reference. The substrate includes a layer of resistive material, such as tantalum aluminum, portions 35 that are individually connected by conductive layers to traces on a flex circuit 60 (see FIG. 6) that, as described more fully below, connects with a controller 52 for operating the drop generators.

Returning to FIG. 2, the individual portions 35 of the resistive layer, hereafter referred to as heat transducers or resistors, are part of what may be collectively referred to as the control layer 44 of the substrate 40, which preferably includes resistor-protective passivation and other sub-layers as described, for example, in U.S. Pat. No. 4,719,477. The requirement for a passivation layer may be minimal in instances where the liquid to be ejected from the chamber is not damaging to the resistor.

It is noteworthy here that the substrate may incorporate CMOS circuit components for permitting the use of multiplexed control signals for firing the drop generators. In addition to the simplified connection with the heat transducers 35 (that is, the elimination of the need for numerous traces directly connected with the heat transducers), the complex control logic afforded by the CMOS circuitry enables, for example, precise metering requirements to be programmed into that circuit and, thus, carried with the device for which the drop generators are fabricated. For instance, if medicinal fluid droplets are to be ejected for an aerosol treatment that requires gradually increasing dosage, the control circuitry can be programmed to fire additional drop generators (increase the flux) with each subsequent use of the device.

A unitary orifice member 48 is fixed to the control layer 44 and is shaped to define for each drop generator an orifice 25 and underlying liquid chamber 33 that is continuous with the orifice. The resistor 35 is selectively driven (heated) with a pulse of electrical current. The heat from the resistor is sufficient to vaporize some of the liquid in the chamber 33, thereby forcing the liquid through the orifice 25 to separate into droplets 36 as described above with respect to FIG. 1.

Each chamber 33 is refilled after each ejection with liquid that flows into the chamber through inlets 54 that are formed through the control layer 44. In a preferred embodiment, the upper surface 56 of the control layer 44 of the substrate is patterned and etched to form the inlets 54 before the orifice member 48 is attached to the substrate, and before a channel 58 is etched in the base 42 of the substrate 40, as described below. (The surface 56 is named "upper" for convenience and with the understanding that the surface 56 may be oriented under the remainder of the control layer 44 when the drop generator is inverted from the orientation shown in FIG. 2.)

Figure 3D:
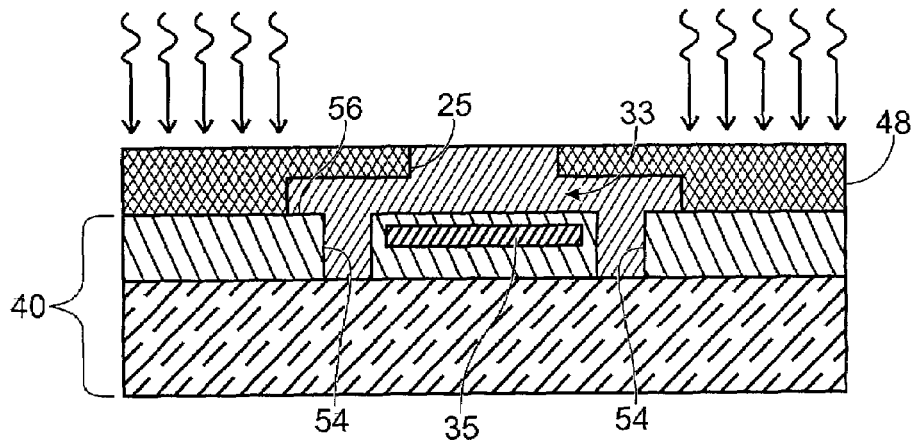
FIG. 3A-3E are cross sectional diagrams illustrating steps in fabricating a drop generator in accordance with a preferred embodiment of the present invention.
Figure 3E:
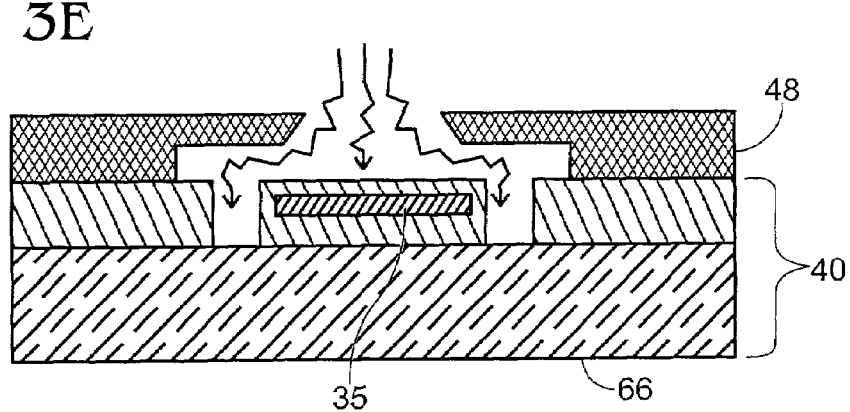
Figure 3A:
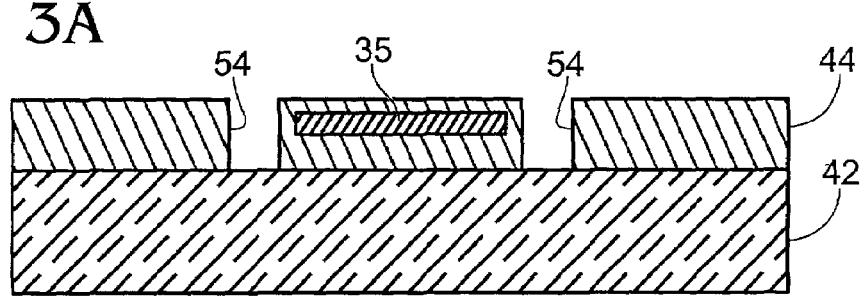

Turning to the particulars of the fabrication steps of the drop generator 20, and with reference to FIG. 3A, shown there is substrate base 42 after it has been processed to carry the control layer 44 that incorporates the previously formed inlets 54.

Figure 3B:
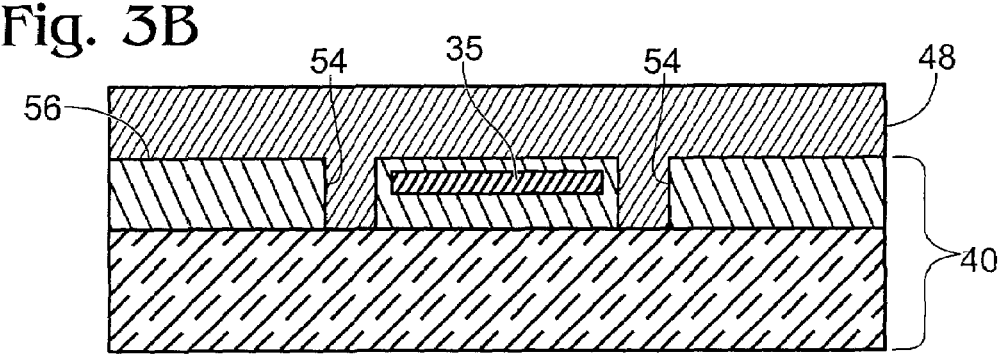

FIG. 3B illustrates the substrate 40 after application of a layer of photoresist material that will comprise the orifice member 48 is applied to the upper surface 56 of the substrate. In one preferred embodiment, the orifice member is a slow-cross-linking polymer that is applied using a conventional spin-coating tool such as one manufactured by Karl Suss KG. In a preferred embodiment, the photoresist material comprises a photo-polymerizable epoxy resin known generally in the trade as SU-8. One example is that available from Micro-Chem Corp. of Newton, Mass. and sold under the name of SU8-10. It will be appreciated, however, that the orifice member could comprise any of a number of photoresist materials that become insoluble in developing solutions after exposure to electromagnetic radiation, such as UV radiation.

The spin-coating process associated with the spin-coating tool allows a planar surface to be formed as the slow-cross-linking polymer fills the inlets 54. An exemplary process for spin coating is to spread a layer of the resist onto a substrate wafer with the spin coating tool set to 70 rpm with an acceleration of 100 rpm/s and a spread time of 20 seconds. The spinning is then stopped with a deceleration of 100 rpm/s and rest for 10 secs. The coated substrate is then spun at 1060 rpm at an acceleration rate of 300 rpm/s for 30 secs to spread the resist over the entire wafer.

Alternative polymer application processes included roll coating, curtain coating, extrusion coating, spray coating, and dip-coating. Those skilled in the art will appreciate that other methods to apply the polymer layers to the substrate exist. The slow cross-linking polymer is made by mixing optical dye (such as orange #3, ~2% weight) into either a photoimagable polyimide or photoimagable epoxy transparent polymer material. By adding dye, the amount of electromagnetic energy required is greater than non-dye mixed material to cross-link the material.

Figure 3C:
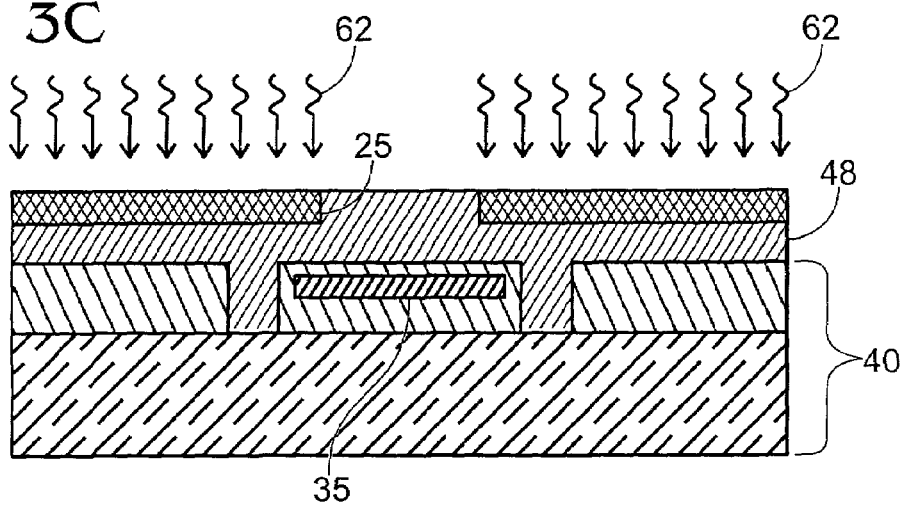

FIG. 3C illustrates the exposure of the layer of the cross-linking polymer material of member 48 with a low dosage of electromagnetic energy (illustrated with arrows 62). In an exemplary embodiment, this step is carried out with a Micralign scanning projection aligner as manufactured by SVG of San Jose, Calif., with an exposure setting of 60.3 mJoules, which is just enough to underexpose and cross link the polymer to a desired depth. In this embodiment, the underexposed, desired depth is shown as double hatching, and can be, for example about 2 μm.

The energy (such as UV radiation) is applied to the orifice member material through a mask (not shown). The mask is a conventional device comprising, for example, a quartz substrate with a layer of semi transparent dielectric, such as ferrous oxide. The mask is patterned with opaque material such as chromium to define (by leaving unexposed) the shape of the orifice 25, which is preferably round.

FIG. 3D illustrates further exposure of the slow-linking polymer material that makes up the orifice member layer 48 with a relatively high dosage of energy that is sufficient to expose and cross link the entire thickness of the layer of polymer 48. This application of energy is masked so that the portion of the liquid chamber 33 that is adjacent to the upper surface 56 of the substrate 40 is not exposed. As shown in FIG. 3D, this portion of the chamber is adjacent to the heat transducer 35 and extends over the junction of the inlets 54 and upper surface 56.

FIG. 3E illustrates the development process in which the unexposed or non-cross linked portions of the orifice member 48, including the portion filling the inlets 54, are removed. An exemplary process uses a 70-second development in N-methyl-2-pyrrolidinone (NMP) at 1 krpm and an 8 second mix of isopropyl alcohol (IPA) and NMP at 1 krpm, then a 10-second rinse with IPA at 1 krpm, and, finally, a 60 second spin at 2 krpm. Such a developing tool is available from Solitec Wafer Processing, Inc., of San Jose, Calif.

Figure 2:
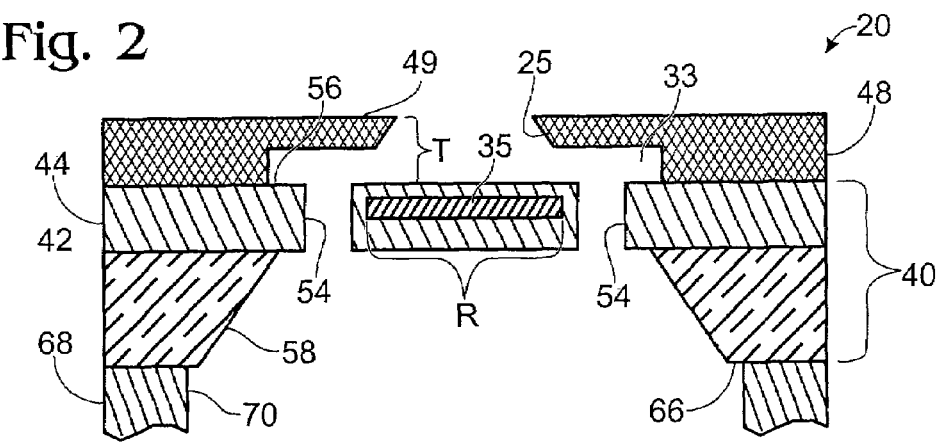
FIG. 2 is an enlarged cross sectional view of a single drop generator formed in accordance with the present invention.

FIG. 2 shows the finished drop generator upon the completion of the development step and after the underside 66 of the substrate is etched with a silicon etch, such as tetramethyl ammonium hydroxide (TMAH) to create the channel 58. The channel 58 is in fluid communication with the liquid inlets 54. Thus, liquid in the channel 58 is able to flow through the inlets 54 and refill the chamber 33 after each ejection of the liquid from the chamber.

As noted above, the size of the heat transducer 35 and the thickness of the chamber 33 are designed to establish the desired ratio T/R. The dimension "T," as noted above, represents the thickness of the chamber 33 and is measured from the upper surface 56 of the control layer (the upper surface 56 representing the liquid/solid interface in the chamber 33) to the outer surface 49 of the of the orifice member 48 (FIG. 2). The dimension "R" is also shown in FIG. 2 and defined above. In a preferred embodiment, the ratio T/R is selected to be less than about 0.75 and, most preferably about 0.35. Thus, for a square-shaped heat transducer having an area of 144 μm², (hence, an "R" value of 12 μm) the most preferred chamber height "T" is about 0.35 times 12, or about 4 μm.

It is noteworthy here, that the ratio T/R, albeit a useful design parameter, is not the only way to arrive at the chamber-size-to-resistor-energy relationship underlying this invention. It will be appreciated, for example, that the heat transducer area correlates to the energy density of the resistor (heat transducer), and the chamber/resistor relationship may be expressed in terms of, for example, a chamber height to transducer energy density value that is required for ejecting the liquid from the chamber such that the liquid is separated into droplets in the desired volumetric range (in the tens of femtoliters or less). Also, it is contemplated that drop generators fabricated with a ratio T/R of greater than 0.75 (up to about 1.0) would also provide the femtoliter-sized droplets of interest here.

Figure 6:
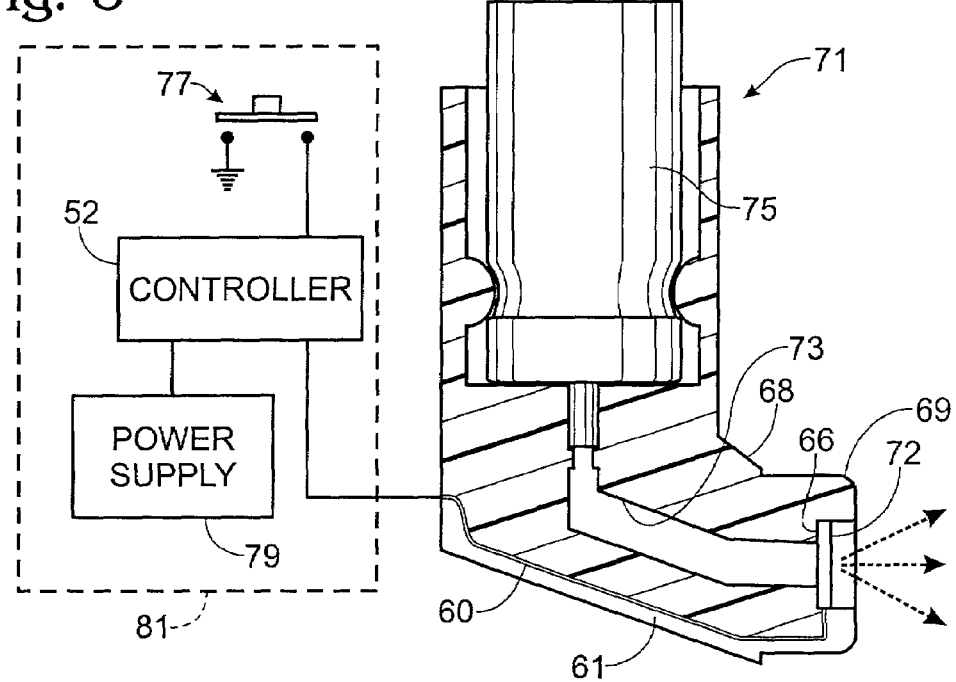
FIG. 6 is a diagram, partly in section, illustrating how drop generators formed in accordance with the present invention may be used for the purpose of generating droplets that are entrained in an aerosol.

Liquid may be provided to the channel 58 in any of a number of ways. For example, the substrate undersurface 66 may be attached to the outer surface of a body 68 of a device that carries a reservoir of liquid (See FIG. 6). The body surface is configured with several conduits 70 (one of which is shown in FIG. 2), each conduit 70 aligning with a channel 58 for directing the liquid from the reservoir to the channel. As noted above, a substrate can carry many drop generators 20, several of which can be fluidically coupled to the linear channel 58 in the substrate, and the substrate can carry several of such channels. The overall device (substrate with multiple drop generators) can be considered a drop generator head 72 (FIG. 6).

Figure 4:
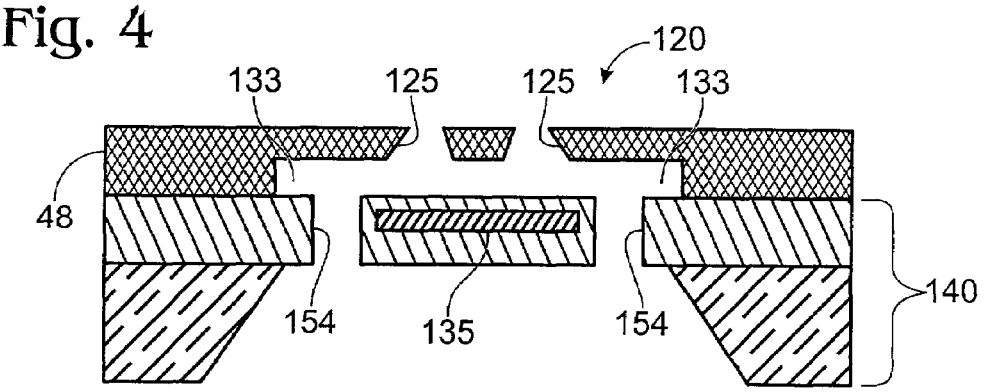
FIG. 4 is a cross sectional diagram illustrating a drop generator made in accordance with another preferred embodiment of the present invention.

FIG. 4 is a cross sectional diagram, similar to FIG. 2, but illustrating a drop generator made in accordance with another preferred embodiment of the present invention. This drop generator 120 includes a substrate 140 and heat transducer 135 as described above. In this embodiment, however, the chamber 133 is in fluid communication with more than one orifice 125. For instance, four orifices 125 arranged around the center of the chamber (only two such orifices appearing in FIG. 4) may be employed. In this embodiment, the heat transducer 135 is a unitary member so that there is one heat transducer for each chamber as was the case in the prior-described embodiment. The unitary transducer 135 is activated and the resultant vapor bubble forces the chamber contents through more than one orifice, which separates the liquid into multiple droplets. The term "unitary" as used here is intended to mean that the heat transducer 135 functions as a unitary member. For instance, it is contemplated that the resistive components of the heat transducer 135 may be spit or otherwise segmented for greater thermal efficiency.

Inasmuch as the multiple-orifice embodiment of FIG. 4 is constructed with the low T/R ratio as described above, there will occur further separation of the droplets as they emerge from the individual orifices 125. Thus, this multiple-orifice embodiment has the effect of multiplying the droplet flux (relative to a single-orifice embodiment) produced each time heat transducer is activated.

Figure 5:
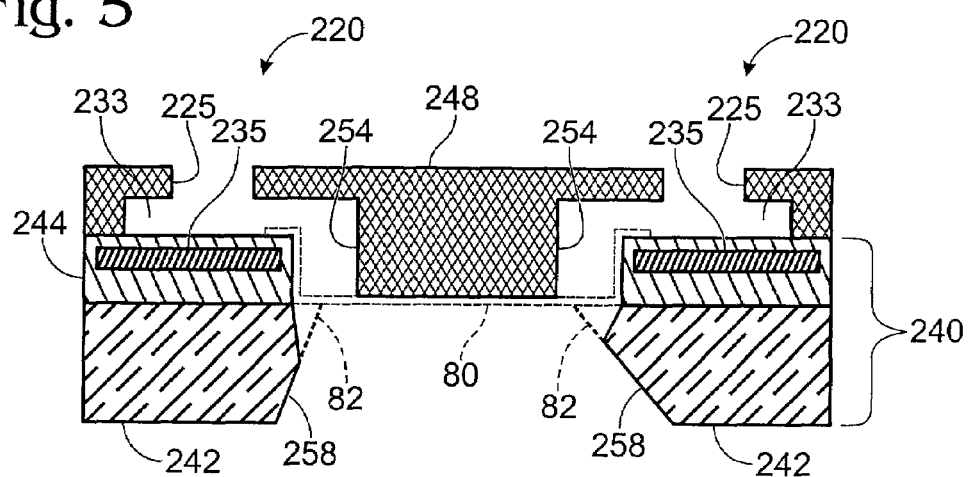
FIG. 5 is a cross sectional diagram illustrating a drop generator made in accordance with another preferred embodiment of the present invention.

A cross sectional diagram of another possible configuration for drop generators made in accordance with the present invention is shown in FIG. 5. In this embodiment, pairs of heat transducers 235 are located in the substrate so that they are on opposing sides of the channel 258 that is etched in the base 242 of the substrate 240. The control layer 244 is initially applied so that the layer of resistive material making up transducers 235 is patterned to define opposing pairs of transducers on opposite edges of the channel 258. The conductive traces to and from the transducers 235 are arranged so they do not span the space between opposing transducers.

The control layer 244 is etched to define a slot between each pair of transducers 235 so that as the photoimageable orifice member 248 is applied, it covers the transducers and fills the slot. The orifice member 248 is then exposed and developed as described above to define the chambers 233 and orifices 225. As shown in FIG. 5, the spaces between the orifice member 248 and transducers 235 define the liquid inlets 254.

In one preferred embodiment, a protective layer, such as a plasma-applied tetraethoxysilane (TEOS) oxide is applied to cover the top surface of the substrate base 242 before the orifice member material is applied. This protective layer is shown in dashed lines 80 in FIG. 5 and is shaped to cover the slot between the two transducers 235 with slight overlap onto the control layer 244 as shown. The orifice member material 248 is applied over the protective layer and shaped as mentioned earlier.

The protective layer 80 is in place while the channel 258 is etched a first time. This long term "bulk" TMAH etching through the base 242 can leave somewhat uneven results. In this regard, the illustrated extensions 82 of the channel walls represent those walls after the first etch of the channel 258. If the first etch were the only one, it can be seen that the opposing inlets 254 would be unequal in size; specifically, the gaps between the base 242 and orifice member 248 are unequal, which would lead to different flow rates of liquid from the channel 258 to the chambers 233.

The present embodiment, however, includes a second TMAH etch of the base 242 (for finishing the channel 258) after the protective layer 80 is removed via, for example, a buffered oxide etchant (BOE). This exposes the silicon surfaces of the substrate base 242 by an extent such that the second TMAH etch equalizes the gaps between the base 242 and orifice member 248 so that the liquid flow through the inlets 254 to the chambers 233 is substantially uniform for all of the drop generators. As before, each drop generator 220 is configured to have the desirable T/R ratio as described above.

It is contemplated that the thermal generation of droplets for aerosols in accordance with the present invention may be carried out by other drop generator configurations. For instance, drop generators made with laser ablated orifice members, such as described in U.S. Pat. No. 5,305,015, hereby incorporated by reference, would be suitable, provided that the relationship between the chamber thickness and transducer size (energy) described above were maintained.

Similarly, drop generators constructed along the lines of those described in U.S. Pat. No. 5,608,436 (hereby incorporated by reference) would also suffice. Those drop generators include a polymeric barrier layer that defines part of the chambers and resides between the upper layer of the substrate and a thin metal orifice plate. Alternatively, the orifice plate may be formed of polymeric material that has been laser ablated to form the orifices as described in U.S. Pat. No. 5,305,015 (hereby incorporated by reference). In such constructions, the orifice plate and/or barrier layer is made to be very thin (these two components can be considered equivalent to the orifice member described above) so that the desired T/R relationship is present.

With respect to any of the above-described embodiments it is important to keep in mind that for a relatively large thickness dimension "T," the desired ration T/R can still be met by the use of a correspondingly large transducer area. In other words, both terms of the ratio are variable as needed to meet the required T/R ratio as well as any other design constraints.

As mentioned above, the present invention provides a thermally efficient drop generator for creating femtoliter-size droplets 36 (FIG. 1) that, as an example, are suitable for entrainment in an aerosol for effective pulmonary delivery. In the present embodiment, this is accomplished via an inhaler 71 such as depicted in FIG. 6. One embodiment of such an inhaler includes a body 68 having a receptacle in which fits a supply 75 of medicinal liquid (or any liquid-based biological and chemical substances as mentioned above).

The supply 75 is coupled, as by a needle and septum interconnection, to a conduit 73 in the body so that the liquid in the supply is directed to the drop generator head 72 that carries the multiple drop generators as described above in connection with FIG. 2. Preferably, the conduit and drop generator head are primed (as by applying suction to the orifices in the head) upon manufacture or by the user before the inhaler is operated to eject drops as described next.

The above-mentioned flex circuit 60 may be bonded, for example, to the inhaler 71 in a correspondingly shaped recess 61 in the body 68. That circuit connects the heat transducers of the drop generators with suitable conditioned control signals from a controller 52, which is part of the inhaler control system 81. The control system 81 includes the controller 52 that is provided with a power supply 79 and operator switch 77. The controller is an integrated circuit that responds to the switch signal by directing to the head 72 controlled current pulses for firing the drop generators as required. It will be appreciated that the control system can be configured in any of a number of ways and, most preferably, integrated with the body of the inhaler.

The drop generator head 72 is preferably located at the mouthpiece 69 of the inhaler. The recess 61 or other mechanisms may be used for providing an air stream during inhalation so that the droplets become entrained in the air.

It will be appreciated that the control system 81 and arrangement of the drop generator head 72 (that is, so that the droplets produced by the head 72 are immediately propelled into the surrounding air) provides for both precise metering of the amount of droplets ejected and of the amount of liquid expelled, as well as the generation of suitably small droplets. That is, the expulsion of the liquid from the chamber need not be accompanied with other mechanisms for reducing the volume of ejected liquid to suitably small droplets.

Even though the foregoing description has focused on the production of droplets suitable for aerosol delivery of the droplets to the alveoli, it will be appreciated that such small droplets can be generated for other applications. The drop generators of the present invention could be incorporated with supplies of liquids suitable for scent delivery, dispensing precisely controlled amounts of pesticides, paints, fuels, etc.

Thus, having here described preferred embodiments of the present invention, it is anticipated that other modifications may be made thereto within the scope of the invention by individuals skilled in the art. Thus, although preferred and alternative embodiments of the present invention have been described, it will be appreciated that the spirit and scope of the invention is not limited to those embodiments, but extend to the various modifications and equivalents as defined in the appended claims.

The invention claimed is:

1. A method of generating droplets, comprising the steps of:
   providing a supply of liquid;
   filling chambers with some of the liquid;
   providing a planar heat transducer within each chamber;
   instantaneously heating the liquid in the chambers by an amount sufficient to produce a vapor bubble in each chamber that propels the liquid from the chamber through an orifice and along a trajectory, and
   orienting the planar heat transducer in a plane that is substantially perpendicular to the trajectory and spaced sufficiently near the orifice so that the propelled liquid separates into two or more droplets upon exiting the orifice.

2. The method of claim 1 including the step of configuring each chamber so that each droplet has a volume of less than 100 femtoliters.

3. An inhaler, comprising:
   a body including a mouthpiece;
   a supply of liquid carried in the body;
   a drop generator head mounted to the body in fluid communication with the liquid and having a plurality of chambers therein, each chamber receiving some of the liquid and opening to surrounding air; and
   a plurality of heat transducers, one heat transducer residing in each chamber and controllable for instantaneously heating the liquid in the chamber by an amount sufficient to produce a vapor bubble in the chamber for propelling the liquid from the chamber in the form of droplets, each droplet having a volume of less than 100 femtoliters, thereby to facilitate aerosol delivery of the droplets to the alveoli of a user of the mouthpiece; and
   wherein each heat transducer has an area and is mounted adjacent to an upper surface in the chamber, and the drop generator includes an orifice opening through an outer surface of the drop generator head, and wherein a distance between the upper surface of the chamber and the outer surface is less than 0.75 times the square root of the area of the heat transducer residing in that chamber.

4. The inhaler of claim 3 wherein a ratio of the chamber thickness to the square root of the transducer area is less than 0.50.

5. The inhaler of claim 3 wherein a ratio of the chamber thickness to the square root of the transducer area is about 0.35

* * * * *

UNITED STATES PATENT AND TRADEMARK OFFICE
CERTIFICATE OF CORRECTION

| | |
|---|---|
| PATENT NO. | : 7,594,507 B2 |
| APPLICATION NO. | : 09/761287 |
| DATED | : September 29, 2009 |
| INVENTOR(S) | : Colin C. Davis |

It is certified that error appears in the above-identified patent and that said Letters Patent is hereby corrected as shown below:

In column 10, line 41, in Claim 5, delete "0.35" and insert -- 0.35. --, therefor.

Signed and Sealed this

Twelfth Day of October, 2010

David J. Kappos
*Director of the United States Patent and Trademark Office*